United States Patent
Benner et al.

(10) Patent No.: US 9,862,983 B1
(45) Date of Patent: *Jan. 9, 2018

(54) RECOMBINASE-BASED AMPLIFICATION WITH SUBSTITUTE NUCLEOTIDES

(71) Applicants: Steven Benner, Gainesville, FL (US); Nilesh Karalkar, Gainesville, FL (US)

(72) Inventors: Steven Benner, Gainesville, FL (US); Nilesh Karalkar, Gainesville, FL (US)

( * ) Notice: Subject to any disclaimer, the term of this patent is extended or adjusted under 35 U.S.C. 154(b) by 120 days.

This patent is subject to a terminal disclaimer.

(21) Appl. No.: 14/746,293

(22) Filed: Jun. 22, 2015

Related U.S. Application Data

(63) Continuation-in-part of application No. 13/789,022, filed on Mar. 7, 2013, now Pat. No. 9,062,336.

(51) Int. Cl.
*C12Q 1/68* (2006.01)
*C12P 19/34* (2006.01)

(52) U.S. Cl.
CPC ............ *C12P 19/34* (2013.01); *C12Q 1/6853* (2013.01); *C12Q 2521/507* (2013.01)

(58) Field of Classification Search
None
See application file for complete search history.

(56) References Cited

U.S. PATENT DOCUMENTS 9,062,336 B1 * 6/2015 Benner .................. C12P 19/34

OTHER PUBLICATIONS

Piepenburg ). et al 2006) DNA Detection Using Recombination Proteins. PLoS Biol 4 (7): e204. doi:10.1371/journal.pbio.0040204, PMC 1475771.
Hoshika, S. et al (2010) Artificial genetic systems. Self-avoiding DNA in PCR and multiplexed PCR. Angew. Chem. Int. Edit, 49, 5554-5557.
Yang, Z., et al (2011) Amplification, mutation, and sequencing of a six-letter synthetic genetic system. J. Am. Chem. Soc. 133, 15105-15112.

* cited by examiner

*Primary Examiner* — David Thomas

(57) ABSTRACT

This invention covers methods for isothermal amplification of DNA, based on the unexpected discovery that primers having, at some positions, adenine substituted by 2-aminopurine or diaminopurine, guanine substituted by inosine, thymine substituted by 2-thiothymine, and cytosine substituted by N4-ethylcytosine are accepted by enzymes used in standard recombinase polymerase assays (RPA). Further unexpected was the discovery that target nucleotides are efficiently amplified in an RPA-like process (hereinafter abbreviated as simply RPA) using substituted primers. The invention also covers RPA-like processes that use substituted primers tagged with oligonucleotides incorporating nucleotides from artificially expanded genetic information systems (AEGIS).

2 Claims, 8 Drawing Sheets

RECOMBINASE-BASED AMPLIFICATION WITH SUBSTITUTE NUCLEOTIDES

CROSS REFERENCE TO RELATED APPLICATIONS

Figure 1:
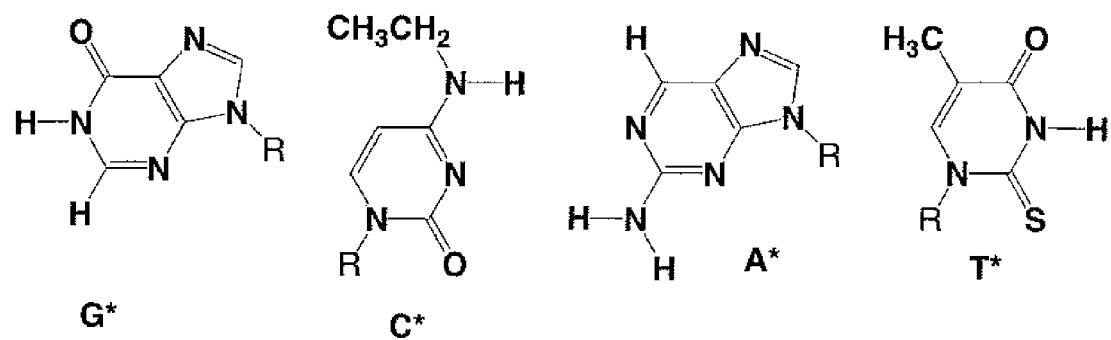

This application is a continuation-in-part of U.S. patent application Ser. No. 13/789,022 (Recombinase-based Amplification With Substitute Nucleotides, filed 7 Mar. 2013), which is copending.

STATEMENT REGARDING FEDERALLY SPONSORED RESEARCH OR DEVELOPMENT

This invention was made with government support under a grant awarded by the United States Defense Advanced Research Project Agency (R0011-11-2-0018). The government has certain rights in the invention.

THE NAMES OF THE PARTIES TO A JOINT RESEARCH AGREEMENT

Not applicable

INCORPORATION-BY-REFERENCE OF MATERIAL SUBMITTED ON A COMPACT DISC.

None

BACKGROUND OF THE INVENTION

(1) Field of the Invention

The field of this invention is nucleic acid chemistry, more specifically nucleic acid amplification technology, and more specifically isothermal amplification methods. This invention relates to processes that, without raising or lowering the temperature, increase the number of copies ("amplify") of a specific "target" DNA or RNA (collectively xNA) sequence.

(2) Description of Related Art

For practical applications in many areas, including the research and DNA- and RNA-targeted diagnostics, methods that amplify nucleic acids without the need to do temperature cycling are highly desirable. Many such "isothermal amplification" methods are known in the art, including those known as "recombinase polymerase amplification" (RPA) [Piepenburg, O., Williams, C. H., Stemple, D. L., Armes, N. A. (2006) DNA Detection Using Recombination Proteins. PLoS Biol 4 (7): e204. doi:10.1371/journal.pbio.0040204. PMC 1475771. PMID 16756388.], rolling circle amplification (RCA), helicase-dependent amplification (HDA), NASBA, and LAMP, among others Isothermal amplification methods frequently do not perform well, however. In many cases, the extent of amplification appears to depend on the specific sequence being amplified or (perhaps) the sequence of probes and/or primers used in the amplification. In some cases, the amplification fails entirely. When the amplification targets more than one target nucleic acid species, isothermal amplification methods often fail.

Essentially no theory explains these and other variable results, although speculation can be found in the public and private art, some of it contradictory, other examples being informal. Without any attempt to be exhaustive, speculative suggestions include the possibility that at low temperatures, non-Watson Crick interactions might cause some of the DNA molecules involved (primer, probe, or analyte) to fold in a way that defeats the amplification process. Others have suggested that high temperatures must be regularly traversed to avoid an (often unknown) intra- or intermolecular interaction from capturing the system as an artifact. Primer-primer interactions have been invoked to explain failure of various isothermal amplification systems, especially when is multiplexing is attempted.

None of these explanations are established. Few data allow us to prefer one over the other. As a consequence, the art contains no clear guidance as to what experiments might be tried to overcome these problems, and to generate reliable procedures of performing isothermal amplification for all target sequences and, especially, for multiple (more than one) target sequences.

BRIEF SUMMARY OF THE INVENTION

This invention is based on the unexpected discovery that primers ("substituted primers") in which at least some of the A, T, G, and C nucleobases are substituted at some (but not necessarily all) sites (positions) with analogs designated A*, T*, G* and C*, by enzymes that work in the standard recombinase polymerase assay (RPA) known in the art [Piepenburg et al., op. cit]. The preferred substitutions replace adenine by 2-aminopurine or diaminopurine, replace guanine by inosine, replace thymine by 2-thiothymine, and replace cytosine by N4-ethylcytosine. This invention is further based on the unexpected discovery that target nucleotides are indeed amplified in an RPA-like process (hereinafter abbreviated as simply RPA) using these substituted primers. Further, this invention is based on the discovery that RPA-like processes where its substituted primers are tagged with oligonucleotides incorporating nucleotides selected from as artificially expanded genetic information system (AEGIS, herein defined) also perform well.

BRIEF DESCRIPTION OF THE SEVERAL VIEWS OF THE DRAWING(S)

Drawing 1. FIG. 1. The presently preferred nucleobases analogs that substitute for G, C, A, and T in the substituted primers, where R is the point of attachment to the oligonucleotide.

Figure 2:
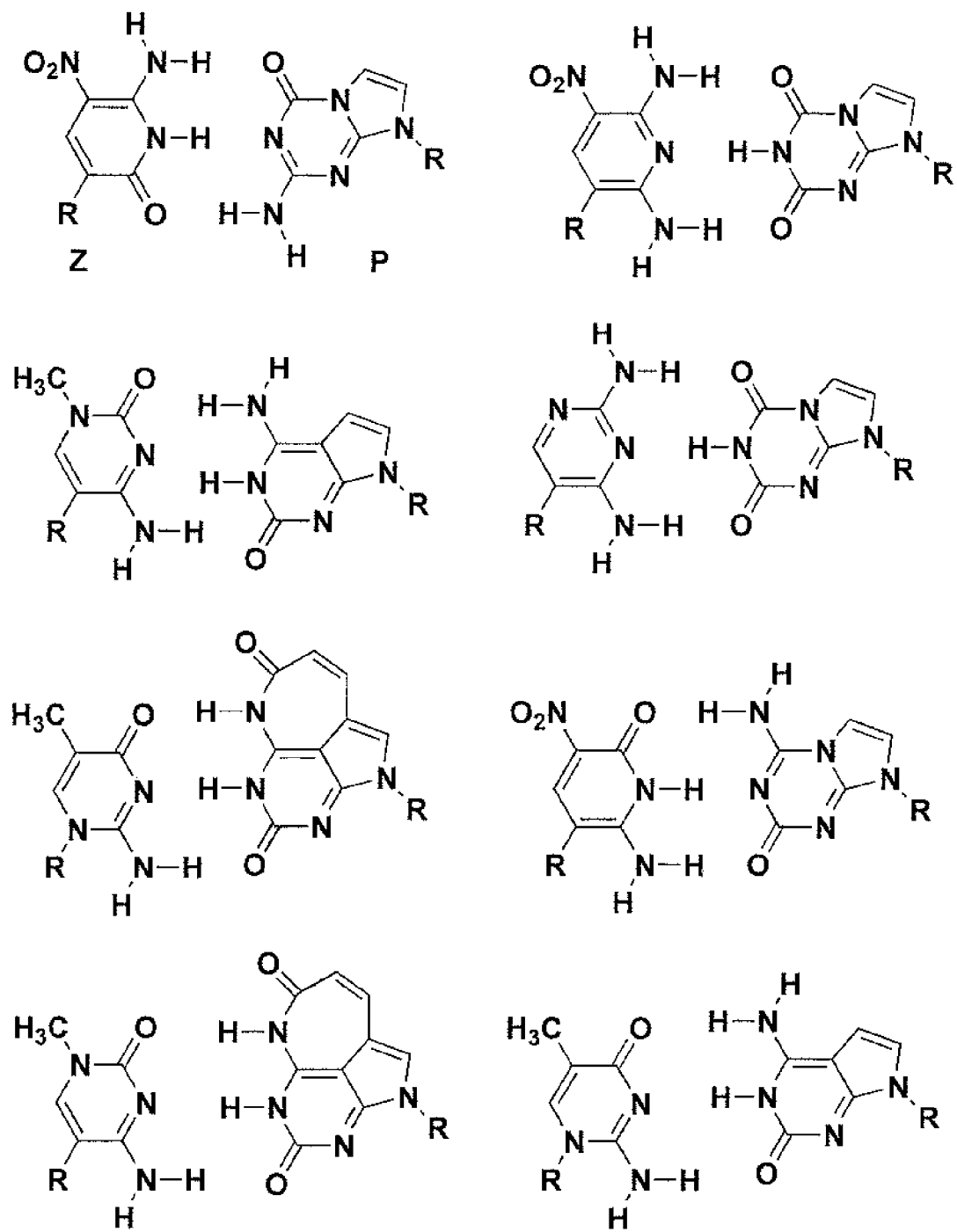

Drawing 2. FIG. 2. The presently preferred components selected from an artificially expanded genetic information system, where R is the point of attachment to the oligonucleotide. This picture also defined the Watson-Crick complementarity between the two nucleotides, and teaches, for each pair, that if one member of the pair is present in the template, then the other must be present in the mixture as the 2'-deoxynucleoside triphosphate.

Figure 3:
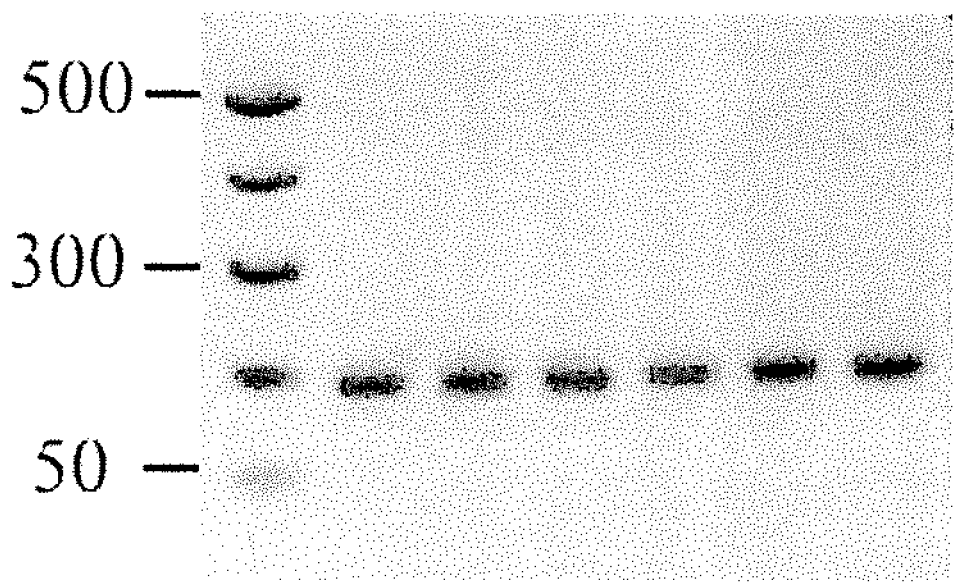
Figure 4:
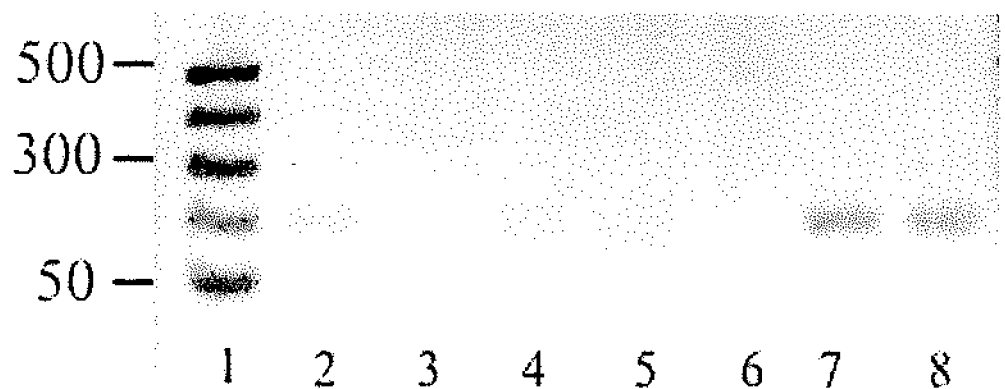
Figure 5:
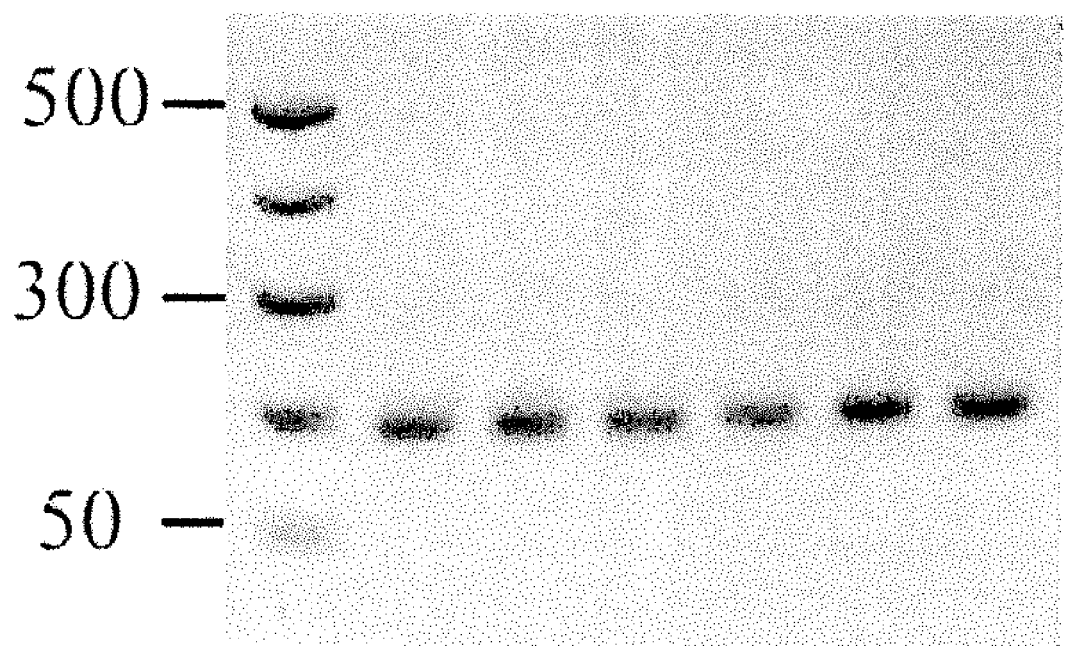

Drawing 3. FIG. 3. Data from Example 1.
Drawing 4. FIG. 4. Data from Example 2.
Drawing 5. FIG. 5. Data from Example 3.
Drawing 6. FIG. 6A, 1-7. Schematic for the synthesis of a tricyclic form of 7-deaza-isoguanosine as its 2'-deoxyribonucleoside, and its triphosphate.

Drawing 7. FIG. 6B, 8-12. Schematic for the synthesis of a tricyclic form of 7-deaza-isoguanosine as its 2'-deoxyribonucleoside, and its triphosphate.

Figure 6A:
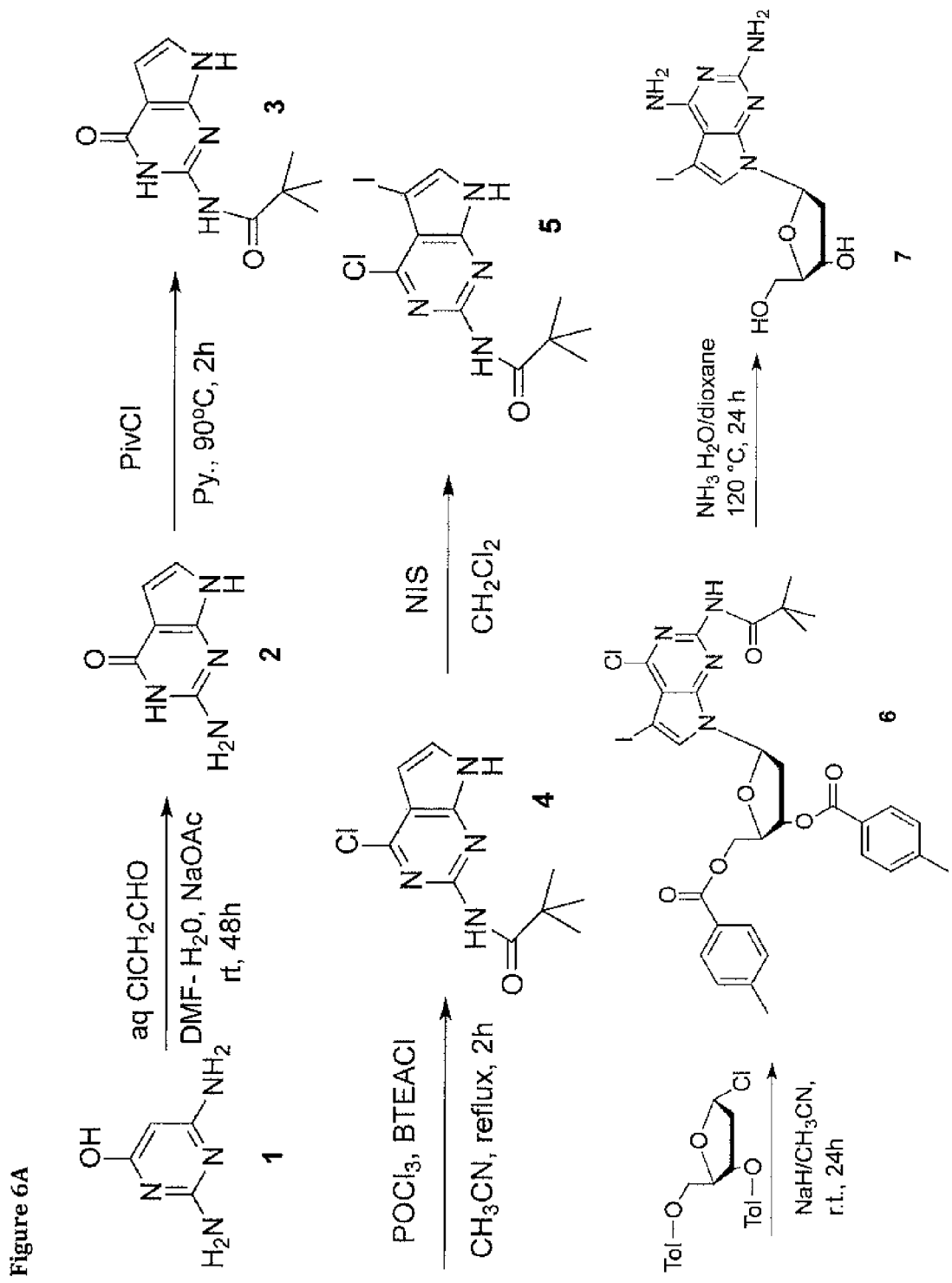
Figure 6B:
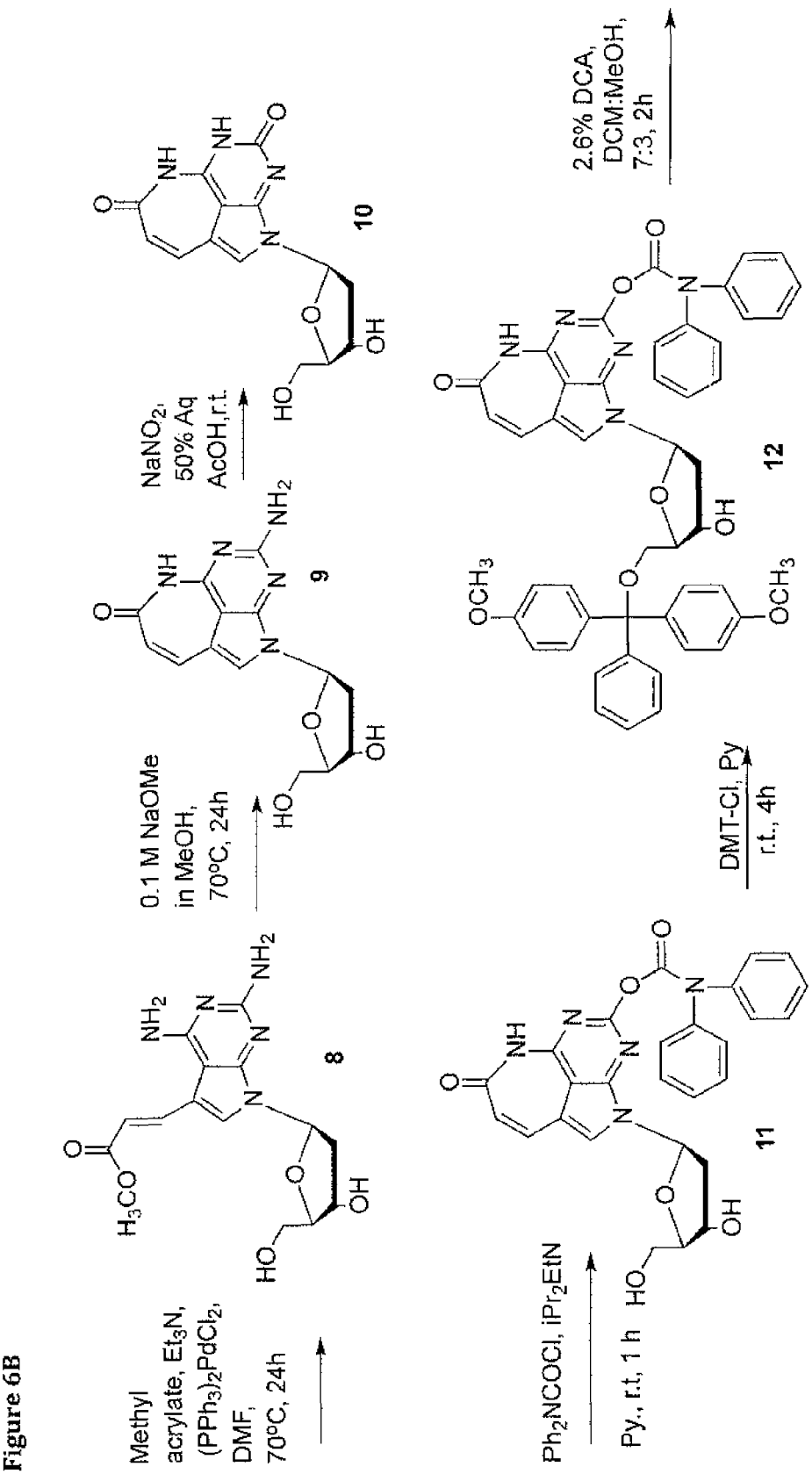
Figure 6C:
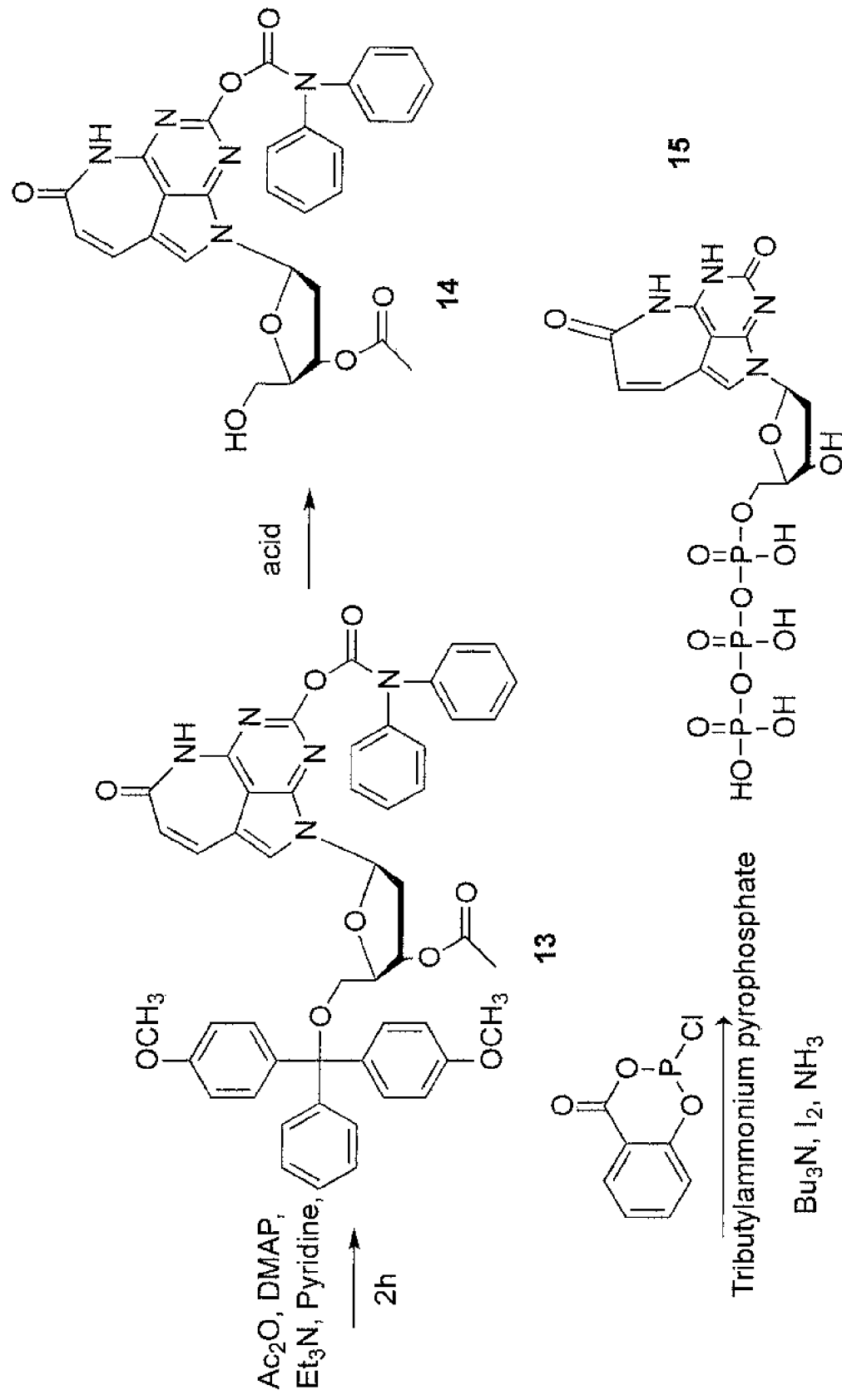

Drawing 8. FIG. 6C, #13-15 Schematic for the synthesis of a tricyclic form of 7-deaza-isoguanosine as its 2'-deoxyribonucleoside, and its triphosphate.

DETAILED DESCRIPTION OF THE INVENTION

1. Narrative

For application, oligonucleotides were synthesized by solid phase automated synthesis, as described in the following two references, which are incorporated in their entirety herein.

Hoshika, S., Leal, N., Chen, F., Benner, S. A. (2010) Artificial genetic systems. Self-avoiding DNA in PCR and multiplexed PCR. *Angew. Chem. Int. Edit.* 49, 5554-5557

Yang, Z., Chen, F., Alvarado, J. B., Benner, S. A. (2011) Amplification, mutation, and sequencing of a six-letter synthetic genetic system. *J. Am. Chem. Soc.* 133, 15105-15112

The examples show that sequences of DNA chosen from viral targets (influenza and HIV, presented as short DNA segments that simulated the live RNA viruses) can be isothermally amplified using an RPA-like architecture and substituted primers. For this purpose, a commercially available RPA kit was purchased from TwistDx. Visualization of the isothermal amplification products was done by Agarose gel electrophoresis.

The sequences of the amplimers and the primers are shown in Table 1. Standard nucleotides are indicated by G, A, C, and T. Substituted nucleotides are indicated by G*, A*, C*, and T*, respectively. These examples target a region of the influenza A virus (in its DNA form) and the Gag region of HIV (also in its DNA form).

TABLE 1

| | Amplimer |
|---|---|
| Influenza A SEQ ID 1 | CTTGAGGCTCTCATGGAATGGCTAAAGACAAGACCAAT CCTGTCACCTCTGACTAAGGGGATTTTGGGGTTTGTGT TCACGCTCACCGTGCCCAGTGAGCGAGGACTGCAGCGT AGACGCTTTGTCCAAAATG |
| HIV-gag SEQ ID 2 | GGACAtCAaGCAGCcATGCAAATGTTAAAAGAgaccat caatgaggaagctgcagactgggataggttacatccag tgcatgcagggccaattccaccagGCCAGATGAGaGAA CCAAGGGGAAGTGACATAGCA |

TABLE 2

| | Sequence |
|---|---|
| Flu-RPA3-Fp1 SEQ ID 3 | CTTGAGGCTCTCATGGAATGGCTAAAGACAAGACC |
| Flu-RPA3-SA-Fp1 SEQ ID 4 | CTTGAGGCTCTCATGGAATGGCTAAAGAC AA*G*A*C*C |
| Flu-RPA3-AESA-Fp1 SEQ ID 5 | CTA PTC CPC CAP CPA PC CTTGAGGCTCTCATGGAATGGCTAAAGAC AA*G*A*C*C |
| Flu-RPA3-Rp1 SEQ ID 6 | CATTTTGGACAAAGCGTCTACGCTGCAGTCC |
| Flu-RPA3-SA-Rp1 SEQ ID 7 | CATTTTGGACAAAGCGTCTACGCTGCA*G*T*C*C |
| Flu-RPA3-AESA-Rp1 SEQ ID 8 | CAG PAA GPG GTP GPT PG CATTTTGGACAAAGCGTCTACGCTGCA*G*T*C*C |

TABLE 2-continued

| | Sequence |
|---|---|
| HIV-gag-FP1 SEQ ID 9 | GGACAtCAaGCAGCcATGCAaATGTTAAAAGAG |
| HIV-gag-SA-FP1 SEQ ID 10 | GGACAtCAaGCAGCcATGCAaATGTTA AA*A*G*A*G |
| HIV-gag-AESA-FP1 SEQ ID 11 | CTA PTC CPC CAP CPA PC GGA CAt CAa GCA GCc ATG CAa ATG TTA AA*A* G*A*g |
| HIV-gag-RP1 SEQ ID 12 | TGCTATGTCACTTCCCCTTGGTTCTCTCATCTGGC |
| HIV-gag-SA-RP1 SEQ ID 13 | TGCTATGTCACTTCCCCTTGGTTCTCTCA TC*T*G*G*C |
| HIV-gag-AESA-RP1 SEQ ID 14 | CAG PAA GPG GTP GPT PG TGC TAT GTC ACT TCC CCT TGG TTC TCT CAT C*T*G* G*C |

2. Examples

Example 1: Jump Start Reaction to Generate Double Stranded Target DNA

In this example, we prepared the target molecules to test RPA-like isothermal amplification of influenza and HIV sequences with substituted primers.

Single-stranded amplimers containing only standard nucleobases were obtained from Integrated DNA Technologies (IDT, Coralville Iowa). The target DNA was introduced in double-stranded form. This was prepared by PCR amplification using the standard primers (Table 2) and single stranded amplimer (Table 1) using Jump Start polymerase and the following recipe.

A PCR (total volume 50 μL) was performed in Jumpstart buffer (Sigma 1×, 10 mM Tris-HCl, pH 8.3 at 25° C., 50 mM KCl, 1.5 mM $MgCl_2$, and 0.001% gelatin) with the indicated forward and reverse primers (0.25 μM) and dNTPs (0.2 mM), Jumpstart Taq DNA polymerase (0.02 units) and the single-stranded amplimer (0.1 μM). Additional $MgCl_2$ (1 mM) was added to the reaction. The mixture was incubated in a thermal cycler at 95° C. for 1 min, followed by 35 cycles at 95° C. for 30 sec; 56° C. or 60° C. for 30 sec and 72° C. for 1 min, with a final extension at 72° C. for 5 min. The reactions were run in triplicate, and the products were recovered using PCR cleanup columns and used in RPA reactions. The results are shown in FIG. 3.

Example 2: Quantitation of DNA

A solution of DNA (1 μL) was prepared in distilled water (100 μL) and its absorbance at 260 nm ($A_{260}$) was measured. For influenza A as a target, the $A_{260}$ was 0.010. With an extinction coefficient of 50, this corresponds to 50 ng of DNA/μL. For HIV as a target, the $A_{260}$ was 0.009 after a 1/200 dilution, and the PCR product was quantitated to be 90 ng/μL. To decrease the number of copies of the template to ~1000, each of the samples was diluted 100,000 fold. The reactions were set up as described above and incubated at 38° C.

Setting up the RPA (Control) and RPA-Like Reactions

Reactions were targeted to amplify 1 μL of PCR product after dilution, as follows:

Control reaction: A 1/10 dilution of the control DNA (provided in the kit from TwistDx) was made. The reaction was setup as follows:
1. A 1/10 dilution of the positive control DNA was prepared (10 μL, in dH$_2$O).
2. Primer solution (8 μL) was added to a fresh 1.5 ml micro centrifuge tube.
3. Then added was 29.5 μL of rehydration buffer to the primer solution. The mixture was briefly vortexed and spun.
4. Then added was 10 μL of the diluted positive control DNA to the solution. The mixture was briefly vortexed and spun.
5. This mixture was added to a freeze-dried TwistAmp™ "Basic Reaction Pellets" (TwistDx).
These contain polymerases and other components required for the classical RPA reaction, and are mixed with the solution by pipetting up and down until the entire pellet was suspended.
6. The reaction was started by adding 2.5 μL 280 mM of magnesium acetate, followed by thorough by vortexed. The tubes were placed in the heating block (38° C.) and incubated for 4 minutes.
7. After 4 minutes, samples were vortexed and returned to the block.
8. The incubation was continues for 40 minutes.
The following were used as Test Reactions:
1. Mixtures containing target influenza DNA and primers, and primers alone were set up as described above. Forward and reverse primers built with standard nucleotides were added (2.4 μL), followed by 29.5 μL rehydration buffer.
2. Water was added to each tube to make the total reaction volume ~47.5 μL.
3. The tubes were vortexed and the reaction mixture was transferred to the TwistAmp™ Basic Reaction Pellets. This was transferred back to the 1.5 mL eppendorf tubes.
4. 2.5 μL of 280 mM of magnesium acetate was added to the cap of the tube. The tubes were vortexed, centrifuged and immediately transferred to a heating block (38° C.) and incubated for 4 minutes.
5. After 4 minutes, samples were vortexed and returned to the block.
6. Continued the incubation for 40 minutes.
The results are shown in FIG. 4. At the end of 40 minutes incubation, the samples were diluted 4 fold and extracted by using phenol:chloroform to remove all proteins (recommended by manufacturer) as the recombinant proteins and polymerase in the reaction retard the migration of the amplified DNA. The extracted samples were ethanol precipitated with sodium acetate (3M, 1/10$^{th}$) and incubated overnight at −20° C.
The samples were resuspended in water and run on a 2.5% agarose gel. As seen in FIG. 4, control DNA is amplified with control primers (Lane 2). No signal is obtained in Lane 3 in the absence of magnesium acetate. With influenza target DNA and standard primers, faint bands were observed in both the presence and absence of target influenza DNA (Lanes 4 and 5). With HIV target DNA, signal was not observed in the absence of magnesium acetate (Lane 6), however, distinct bands were observed in the presence and absence of target HIV DNA (Lanes 7 and 8).

Example 3: RPA-Like Amplifications with SAMRS and AEGIS-SAMRS Hybrid Primers

A master mix containing forward and reverse primers (2.4 μL each, 480 nM final concentrations) was reconstituted in rehydration buffer (provided by TwistDx), as follows:

| | |
|---|---|
| Primer F (standard, SAMRS or AEGIS-SAMRS oligonucleotides): | 2.4 μL |
| Primer R (standard, SAMRS or AEGIS-SAMRS oligonucleotides): | 2.4 μL |
| Rehydration buffer: | 29.5 μL |
| Water: | 11.2 μL |

This was placed into pre-prepared tubes (TwistDx) containing the freeze dried RPA pellets, which contain polymerases and other components required for the classical RPA reaction. Then, aliquots (22.75 μL) were transferred to two TwistDx Eppendorf tubes to set up positive reactions and negative control. To create the positive, target DNA template (0.8 μL) was added to one aliquot.

Water in equal amounts was added to the other aliquots to create the negative control. To create a reference standard for subsequent gel electrophoresis, DNA solution (0.8 μL) was diluted into water lacking primers and magnesium acetate. For reactions supported by AEGIS-SAMRS primers, dZTP (20 μM) was added. The mixtures were then incubated at 38° C.

The results are shown in FIG. 5. As seen in the experiment with the Influenza A target, a product was obtained using standard primers as a faint band following electrophoresis on an agarose gel (2.5%) stained with ethidium bromide (lane 2). The bands in lane 3 were assigned to the primers and their dimers, as target was absent in the reaction mixture.

With the influenza A DNA target, the primers with SAMRS modifications gave a stronger and more clearly defined product band having the size expected for the amplification product (lane 4). In the absence of target, only diffuse product were seen (lane 5). With the AEGIS-SAMRS hybrid primers, the only product observed was a well-defined band having the expected size (lane 6). The slower electrophoretic mobility indicates that the external AEGIS segments of the primers were also copied. No signal was seen in the negative control (lane 7), which contained AEGIS-SAMRS primers alone. This suggests that the presence of SAMRS and AEGIS-SAMRS nucleotides in the primers prevents the artifacts and allows for the reactions to be efficient in presence of a target. The HIV gag DNA target gave a good product signal with the standard primers (lane 2). A diffuse product is for primer alone (lane 3). With the SAMRS primers and DNA target (lane 4), a clear and directly sized product is seen; the second band may arise from excess template. The results with SAMRS primer alone are shown in lane 5. However, with the reaction with AEGIS-SAMRS primers and target DNA alone, only a single product having the correct size is seen (lane 6), and no background is seen with the AEGIS-SAMRS primers alone (lane 7).

The results were confirmed using a Luminex assay, with probes attached to beads targeted to regions near the center of the amplicon.

Example 4. Synthesis of a Tricyclic Analog of 7-Deaza-Isoguanosine and its Triphosphate (FIG. 6)

2-Amino-3,7-dihydro-pyrrolo[2,3-d]pyrimidin-4-one (2)

2,4-Diamino-6-hydroxypyrimidine (25.2 g, 200 mmol) was dissolved in DMF (480 mL) and water (80 mL) at room temperature. Sodium acetate (16.6 g, 200 mmol) was added to this solution and the resulting yellow solution was stirred for 1 h. Chloroacetaldehyde (25.3 mL, 200 mmol) was added, and the mixture was stirred for 46 h at room temperature. The reaction mixture was then concentrated by rotary evaporation. The product was triturated with water (20 mL) and recovered by filtration. The filtered solid was digested in refluxing methanol (500 mL) for 2 h, and the mixture was then placed in a refrigerator at 4° C. overnight to yield a product as a precipitate, which was recovered by filtration, washed with EtOAc (4×250 mL) and dried in a vacuum desiccator over $P_2O_5$ (20 g, 133 mmol, 66% yield).

$^1$H NMR (300 MHz, DMSO-d6) ppm 11 (s, 1H), 10.35 (s, 1H), 6.6 (s, 1H), 6.15 (s, 1H), 6.09 (s, 2H)

N-(4-oxo-4,7-dihydro-3H-pyrrolo[2,3-d]pyrimidin-2-yl)pivalamide (3)

A solution of 2-amino-3,7-dihydro-pyrrolo[2,3-d]pyrimidin-4-one (25 g, 166.66 mmol) in pyridine (300 mL) was treated with trimethylacetyl chloride (65.74 mL, 533 mmol) at 90° C. for 2 h, to give a mixture of N(2)-monoacylated and N(2), N(7)-bisacylated material. The solvent was evaporated and the residue was taken up in aqueous ammonia (28% $NH_3$, 42 mL) and MeOH (300 mL), and stirred at room temperature for 30 min, to selectively cleave the N(7)-pivaloyl group. The product precipiates, and the solid was collected by filtration, washed with cold MeOH, and dried on high vacuum (16 g, 68 mmol, 41% yield).

$^1$H NMR (300 MHz, DMSO-d6) ppm 11.82 (s, 1H), 11.58 (s, 1H), 10.8 (s, 1H), 6.9 (d, 1-3.4 Hz, 1H), 6.38 (d, J=3.6 Hz, 1H), 1.2 (s, 9H)

N-(4-chloro-7H-pyrrolo[2,3-d]pyrimidin-2-yl)pivalamide (4)

A mixture of N-(4-oxo-4,7-dihydro-3H-pyrrolo[2,3-d]pyrimidin-2-yl) pivalamide (11 g, 47 mmol), $POCl_3$ (26 mL, 282 mmol), benzyltriethylammonium chloride (21.4 g, 94 mmol), N,N-dimethylaniline (12 mL, 94 mmol), and acetonitrile (104 mL) was heated at reflux for 1 h. The volatiles were removed by rotary evaporation, and the residual oil was slowly added to 800 mL of ice-water (which destroys the remaining $POCl_3$). The pH was adjusted to 4 by dropwise addition of 28% aqueous $NH_4OH$ to generate product as a precipitate, which was collected by filtration, washed with cold water, and purified by silica chromatography (30% ethyl acetate/hexane) to give purified product as a white solid (7 g, 0.27 mol, 58% yield).

$^1$H NMR (300 MHz, DMSO-d6) ppm 12.33 (br. s., 1H), 10.04 (s, 1H), 7.52 (d, 0.1-3.57 Hz, 1H), 6.50 (d, J=3.43 Hz, 1H), 1.20 (s, 9H)

4-Chloro-5-iodo-2-pivaloylamino-7H-pyrrolo[2,3-d]pyrimidine (5)

A solution of compound 4 (5.0 g, 19.84 mmol) and N-Iodosuccinimide (5.35 g, 23.8 mmol) in $CH_2Cl_2$ (100 mL) was stirred at 40° C. for 5 h. The yellow solution was evaporated to an amber residue which was crystallized from MeOH to give yellowish crystals (3.5 g).

$^1$H NMR (300 MHz, DMSO-d6) ppm 1.22 (s, 9H), 7.77 (s, 1H), 10.13 (s, 1H), 12.71 (s, 1H).

4-Chloro-7-[2-deoxy-3,5-di-O-(p-toluoyl)-b-D-erythro-pentofuranosyl]-5-iodo-2-pivaloylamino-7H-pyrrolo[2,3-d]pyrimidine (6)

To a suspension of NaH (60% emulsion in oil, 0.767 g, 17.8 mmol) in dry acetonitrile (400 mL) was added 5 (6.7 g, 17.7 mmol) at room temperature. After incubation for 1 h, 2-deoxy-3,5-di-O-(p-toluoyl)-17-D-erythro-pentofuranosyl chloride (12.1 g, 22.6 mmol) was added to the reaction mixture, which was stirred further for 16 h. The product (5 g) was obtained as a white solid after removal of the solvent on a rotary evaporator and purification by silica gel chromatography (EtOAc/hexanes 1:4).

$^1$H NMR (300 MHz, DMSO-d6) ppm 1.21 (s, 9H), 2.37, 2.39 (2 s, 6H), 2.69-2.75 (m, 1H), 3.19-3.25 (m, 1H), 4.47-4.53 (m, 2H), 4.61-4.67 (m, 1H), 5.77-5.79 (m, 1H), 6.63 (t, 1H, J=6.8 Hz), 7.31, 7.37, 7.84, 7.94 (4 d, 8H, J=8.1 Hz), 7.99 (s, 1H), 10.29 (s, 1H).

7-(2-Deoxy-b-D-erythro-pentofuranosyl)-5-iodo-7H-pyrrolo-[2,3-d]pyrimidine-2,4-diamine (7)

A suspension of compound 6 (3 g, 4.1 mmol) in dioxane (60 mL) and 25% $NH_3/H_2O$ (160 mL) was introduced into an stainless steel pressure bomb and stirred at 120° C. for 24 h. The clear solution was evaporated and the residue was subjected to flash chromatography (silica gel, column, EtOAc:MeOH:$H_2O$, 80:17:3). The main zone was collected and rotavap to a brown color solid of 2 (3 g, 94%).

$^1$H NMR (300 MHz, DMSO-d6) ppm 7.40 (br. s., 2H), 7.01 (d, J=3.6 Hz, 1H), 6.22-6.38 (m, 3H), 5.22 (d, J=2.9 Hz, 1H), 4.27 (br. s., 1H), 3.75 (br. s., 1H), 3.40-3.56 (m, 2H), 2.27-2.42 (m, 1H), 2.05 (dd, J=12.8, 5.7 Hz, 1H)

2,4-Diamino-5-[(E)-1-(methoxycarbonyl)-2-ethenyl]-7-(2-deoxy-b-D-erythro-pentofuranosyl)pyrrolo[2,3-d]pyrimidine (8)

To a solution of 7 (391 mg, 1.0 mmol) in DMF (10 mL) including Et3N (0.28 mL, 2.0 mmol) and $(PPh_3)_2PdCl_2$ (70 mg, 0.1 mmol) was added methyl acrylate (3.62 mL, 40 mmol), and the reaction mixture was heated to 70° C. for 5 h. The solvent was removed in vacuum, and the residue was purified by flash chromatography (silica gel, column, EtOAc:MeOH:$H_2O$, 80:17:3). The main zone was collected and rotavap to a brown color solid of 3 (200 mg).

$^1$H NMR (300 MHz, DMSO-d6) ppm 7.82 (d, 1H, J=15.5 Hz), 7.71 (s, 1H), 6.36 (dd, 1H, J=5.7 and 8.3 Hz), 6.36 (br s, 2H), 6.30 (d, 1H, J=15.5 Hz), 5.82 (br s, 2H), 5.22 (d, 1H, J=3.5 Hz), 5.02 (t, 1H, J=5.8 Hz), 4.31 (m, 1H), 3.77 (m, 1H), 3.68 (s, 3H), 3.55 and 3.49 (m, 1H), 2.38 (ddd, 1H, J=8.3, 5.5, and 13.2 Hz), 2.09 (ddd, 1H, J=5.7, 2.9, and 13.2 Hz)

4-Amino-2-(2-deoxy-b-D-erythro-pentofuranosyl)-2,6-dihydro-7H-2,3,5,6-tetraazabenzo[cd]azulen-7-one (9)

A solution of 8 (1.1 g, 3.148 mmol) in 0.1 M NaOMe in MeOH (157 mL) was heated at 70° C. for 12 h. The reaction mixture was cooled to 0° C., and the resulting precipitate was collected to give 9 as yellow solid. The filtrate was removed in vacuo and the residue was purified by silica gel column eluted with MeOH (25%) in DCM to give additional 9 (1.3 g).

$^1$H NMR (300 MHz, DMSO-d6) ppm 10.08 (d, 1H, J=1.2 Hz), 7.34 (s, 1H), 6.93 (d, 1H, J=12.0 Hz), 6.29 (dd, 1H, J=5.9 and 7.9 Hz), 6.25 (brs, 2H), 5.58 (d, 1H, J=11.6 Hz), 5.26 (d, 1H, J=3.6 Hz), 5.02 (t, 1H, J=5.8 Hz), 4.30 (m, 1H), 3.77 (m, 1H), 3.49 (m, 2H), 2.49 (m, 1H), 2.12 (ddd, 1H, J=6.1, 2.3, and 12.8 Hz).

Synthesis of Compound 10

To a stirred solution of compound 9 (100 mg, 0.315 mmol) in 20% $AcOH—H_2O$ (v/v, 6 mL), was added dropwise a solution of NaNO$_2$ (45 mg, 0.66 mmol) in H$_2$O (1.0 mL) at r.t. The stirring was continued for 1 h. 50 min, and the pH of the dark solution was adjusted to 8.0 with 25% aq NH$_3$ under cold condition. The solid obtained was filtered and dried (50 mg).

HRMS: [M+H]$^+$319.1

Synthesis of Compound 11

To a suspension of 10 (425 mg, 1.336 mmol) in dry pyridine (25 mL) were added diphenylcarbamoyl chloride (557 mg, 2.4 mmol) and N,N-diisopropylethylamine (0.42 mL, 2.4 mmol). The mixture was stirred for 4 h at room temperature, and then poured in the 5% aqueous NaHCO$_3$ (50 mL) and extracted with CH$_2$Cl$_2$ (2×100 mL). The combined CH$_2$Cl$_2$ layers were dried over Na$_2$SO$_4$ and clarified by filtration. The product 11 was then recovered by rotary evaporation and purified by flash chromatography (silica gel, elution with CH$_2$Cl$_2$ followed by CH$_2$Cl$_2$-MeOH step wise from 0 to 4% methanol) to give a brown color foam (350 mg).

HRMS: [M+H]$^+$=514.1721

Synthesis of Compound 12

Compound 11 (350 mg, 0.68 mmol) was dried by co-evaporation with anhydrous pyridine (2×, 15 mL) and dissolved in anhydrous pyridine (25 mL). This solution was treated with dimethoxytrityl chloride (276 g, 0.82 mmol) at room temperature under stirring for 4 h. Water was then added to the mixture and the stirring was continued for 35 min. The mixture was diluted with a 5% aqueous NaHCO$_3$ solution (100 mL) and extracted with CH$_2$Cl$_2$ (2×350 mL). The combined extracts were dried over Na$_2$SO$_4$. The solvent was removed by rotary evaporation, and the product 10 was obtained as an orange-brown foam (400 mg) by purification by flash chromatography (silica gel, eluted with 2:1 to 1:2, hexane: ethyl acetate).

HRMS: [M+Na]$^+$=838.28

Synthesis of Compound 13

12 (0.44 mmol, 400 mg), DMAP (0.25 mmol, 31 mg), Et$_3$N (1.1 mmol, 0.154 mL), and Ac$_2$O (0.528 mmol, 0.049 mL) were added to a solution of dry pyridine (10 mL). The mixture was stirred at room temperature for 2 h. MeOH (1 mL) was added, the mixture was diluted with 100 mL of dichloromethane and extracted with 5% NaHCO$_3$ (50 mL). The aqueous layer was back extracted with dichloromethane (100 mL). The combined organic layers were dried over sodium sulfate, filtered and concentrated by rotary evaporation. The residue was purified by flash chromatography (hexane:ethyl acetate, 2:1 to 1:2) to give product 13 (350 mg).

HRMS: [M+Na]$^+$=880.2953

Synthesis of Compound 14

Compound 13 (350 mg, 0.41 mmol) was dissolved in a mixture (50 mL) of dichloromethane and methanol (7:3). The solution was cooled to 0° C., dichloroacetic acid (0.83 mL, 10.2 mmol) was added, and stirring was continued at 0° C. for 2 h. The mixture was then neutralized with aqueous saturated NaHCO$_3$ (50 mL), and extracted with dichloromethane (100 mL). The resulting organic layer was dried over sodium sulfate, concentrated by rotary evaporation, and the residue was purified by column chromatography (hexane:ethyl acetate 1:2 to 0:1) to give product as a white solid (155 mg).

HRMS: [M+H]$^+$=556.1827

Synthesis of Compound 15

To a solution of compound 14 (0.155 g, 0.28 mmol) in pyridine (5 mL) and dioxane (10 mL) was added a solution of 2-chloro-4-H-1,3,2-benzodioxaphosphorin-4-one (0.085 g, 0.42 mmol) in dioxane (5.0 mL) at room temperature. After incubation for 15 min, a mixture of tributylammonium pyrophosphate in DMF (0.2 M, 4.2 mL, 0.84 mmol) and tributylamine (0.45 mL) was added. After incubating for 20 min, a solution of iodine (0.1064 g, 0.42 mmol) and water (0.315 mL) in pyridine (15.5 mL) was added. After incubating for 30 min, the reaction was quenched by the addition of aqueous Na$_2$SO$_3$ (5%, until color disappears). The pyridine and dioxane were removed by rotary evaporation. The residue was dissolved in a mixture of water and acetonitrile (10 mL each) and kept at room temperature overnight. The product was resolved by reverse phase preparative LC (gradient 25 mM TEAA to 25 mM TEAA: CH$_3$CN (1:1) =5:95 in 38 min, running time 46 min), with the solvents in the fraction containing the product removed by lyophilization. The residue was dissolved in ammonium hydroxide (2 mL), and the solution was stirred at room temperature for 3 h. The solution was injected onto an ion exchange HPLC column. The product (14 mg) was recovered as a yellow solid by lyophilization of fractions collected by gradient elution (water to 1 M ammonium bicarbonate over 32 min; running time 42 min)

HRMS: [M−H]$^+$=556.9881

---

What is claimed is:

1. A process for increasing the number of copies of two complementary DNA strands, wherein said strands are hybridized in the form of a DNA target duplex, wherein said process comprises:
   (a) adding said DNA target duplex to an aqueous mixture that contains a Basic Reaction Pellet that comprises a DNA polymerase, a recombinase, and all other components necessary to support a recombinase polymerase amplification, wherein
   (b) said aqueous mixture also contains 2'-deoxynucleoside triphosphates that complement each nucleotide in the said complementary DNA strands, wherein
   (c) said aqueous mixture also contains substituted primers comprising a first primer that is substantially complementary in sequence to a segment at or near the 3'-end of the first of said DNA strands, and a second primer that is substantially complementary in sequence to a segment at or near the 3'-end of the second of said DNA strands, and where
   (d) within said substituted primer at least one adenine nucleobase in at least one of its 2'-deoxyadenosine nucleotides is substituted by 2-aminopurine or diaminopurine, at least one guanine nucleobase in at least one of its 2'-deoxyguanosine nucleotides is substituted by inosine, at least one thymine nucleobase in at least one of its thymidine nucleotides is substituted by 2-thiothymine, or at least one cytosine in at least one of its 2'-deoxycytidine nucleotides is substituted by N4-ethylcytosine, wherein
   (e) the total number of said substitutions is at least four, wherein
   (f) appended to the 5'-end of one or more of said substituted primers is an oligonucleotide tag that comprises a preselected oligonucleotide that contains one or more nucleotide analogs that carry a nucleobase selected from the group consisting of

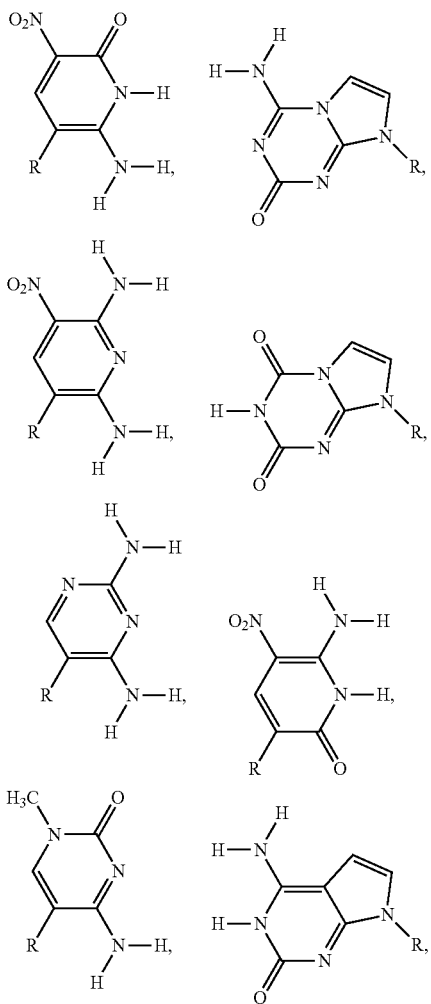

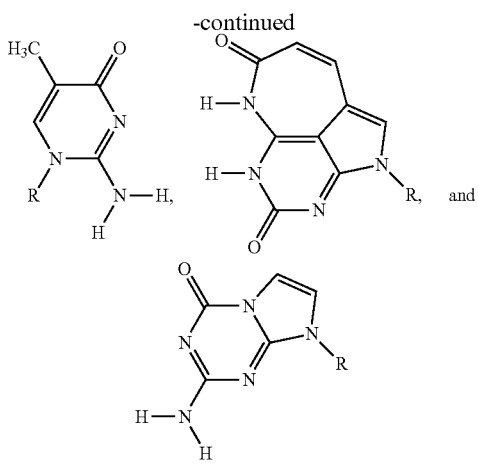

wherein —R indicates the point of attachment to the 2'-deoxyribose of said oligonucleotide tag, and wherein
(g) said aqueous mixture also contains one or more triphosphates of one or more 2'-deoxynucleotides that are complementary to said one or more nucleotide analogs contained by said oligonucleotide tag.

2. The process of claim 1, wherein said preselected oligonucleotide tag contains at least one nucleotide analog that carries a nucleobase selected from the group consisting of

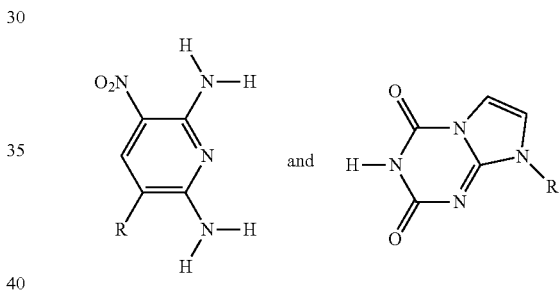

wherein —R indicates the point of attachment to the 2'-deoxyribose of said oligonucleotide tag.

\* \* \* \* \*

SEQUENCE LISTING

```
<160> NUMBER OF SEQ ID NOS: 14

<210> SEQ ID NO 1
<211> LENGTH: 133
<212> TYPE: DNA
<213> ORGANISM: Artificial Sequence
<220> FEATURE:
<223> OTHER INFORMATION: Synthetic

<400> SEQUENCE: 1
cttgaggctc tcatggaatg gctaaagaca agaccaatcc tgtcacctct gactaagggg      60
attttggggt ttgtgttcac gctcaccgtg cccagtgagc gaggactgca gcgtagacgc     120
```

```
tttgtccaaa atg                                                          133
```

<210> SEQ ID NO 2
<211> LENGTH: 135
<212> TYPE: DNA
<213> ORGANISM: Artificial Sequence
<220> FEATURE:
<223> OTHER INFORMATION: Synthetic

<400> SEQUENCE: 2

```
ggacatcaag cagccatgca aatgttaaaa gagaccatca atgaggaagc tgcagactgg        60
gataggttac atccagtgca tgcagggcca attccaccag gccagatgag agaaccaagg       120
ggaagtgaca tagca                                                        135
```

<210> SEQ ID NO 3
<211> LENGTH: 35
<212> TYPE: DNA
<213> ORGANISM: Artificial Sequence
<220> FEATURE:
<223> OTHER INFORMATION: Synthetic

<400> SEQUENCE: 3

```
cttgaggctc tcatggaatg gctaaagaca agacc                                   35
```

<210> SEQ ID NO 4
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: 2-aminopurine
<220> FEATURE:
<221> NAME/KEY: misc_feature
<222> LOCATION: (32)..(32)
<223> OTHER INFORMATION: inosine
<220> FEATURE:
<221> NAME/KEY: misc_feature
<222> LOCATION: (33)..(33)
<223> OTHER INFORMATION: 2-aminopurine
<220> FEATURE:
<221> NAME/KEY: misc_feature
<222> LOCATION: (34)..(34)
<223> OTHER INFORMATION: N4-ethylcytosine

<400> SEQUENCE: 4

```
cttgaggctc tcatggaatg gctaaagaca nnnnc                                   35
```

<210> SEQ ID NO 5
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (8)..(8)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (12)..(12)
<223> OTHER INFORMATION: n = 7-amino-9-(1'-beta-D-2'-

```
         deoxyribofuranosyl)-imidazo[1,2-c]pyrimidin-5(1H)-one
<220> FEATURE:
<221> NAME/KEY: misc_feature
<222> LOCATION: (14)..(14)
<223> OTHER INFORMATION: n = 7-amino-9-(1'-beta-D-2'-
         deoxyribofuranosyl)-imidazo[1,2-c]pyrimidin-5(1H)-one
<220> FEATURE:
<221> NAME/KEY: misc_feature
<222> LOCATION: (16)..(16)
<223> OTHER INFORMATION: n = 7-amino-9-(1'-beta-D-2'-
         deoxyribofuranosyl)-imidazo[1,2-c]pyrimidin-5(1H)-one
<220> FEATURE:
<221> NAME/KEY: misc_feature
<222> LOCATION: (48)..(48)
<223> OTHER INFORMATION: n = 2-aminopurine
<220> FEATURE:
<221> NAME/KEY: misc_feature
<222> LOCATION: (49)..(49)
<223> OTHER INFORMATION: n = inosine
<220> FEATURE:
<221> NAME/KEY: misc_feature
<222> LOCATION: (50)..(50)
<223> OTHER INFORMATION: n = 2-aminopurine
<220> FEATURE:
<221> NAME/KEY: misc_feature
<222> LOCATION: (51)..(51)
<223> OTHER INFORMATION: n = N4-ethylcytosine

<400> SEQUENCE: 5
ctantccncc ancnancctt gaggctctca tggaatggct aaagacannn nc          52

<210> SEQ ID NO 6
<211> LENGTH: 31
<212> TYPE: DNA
<213> ORGANISM: Artificial Sequence
<220> FEATURE:
<223> OTHER INFORMATION: Synthetic

<400> SEQUENCE: 6
cattttggac aaagcgtcta cgctgcagtc c                                 31

<210> SEQ ID NO 7
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (27)..(27)
<223> OTHER INFORMATION: n = 2-aminopurine
<220> FEATURE:
<221> NAME/KEY: misc_feature
<222> LOCATION: (28)..(28)
<223> OTHER INFORMATION: n = inosine
<220> FEATURE:
<221> NAME/KEY: misc_feature
<222> LOCATION: (29)..(29)
<223> OTHER INFORMATION: n = 2-thiothymine
<220> FEATURE:
<221> NAME/KEY: misc_feature
<222> LOCATION: (30)..(30)
<223> OTHER INFORMATION: n = N4-ethylcytosine

<400> SEQUENCE: 7
cattttggac aaagcgtcta cgctgcnnnn c                                 31

<210> SEQ ID NO 8
<211> LENGTH: 48
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (4)..(4)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (8)..(8)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (12)..(12)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (14)..(14)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (16)..(16)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (44)..(44)
<223> OTHER INFORMATION: n = 2-aminopurine
<220> FEATURE:
<221> NAME/KEY: misc_feature
<222> LOCATION: (45)..(45)
<223> OTHER INFORMATION: n = inosine
<220> FEATURE:
<221> NAME/KEY: misc_feature
<222> LOCATION: (46)..(46)
<223> OTHER INFORMATION: n = 2-thiothymine
<220> FEATURE:
<221> NAME/KEY: misc_feature
<222> LOCATION: (47)..(47)
<223> OTHER INFORMATION: n = N4-ethylcytosine

<400> SEQUENCE: 8
cagnaagngg tngntngcat tttggacaaa gcgtctacgc tgcnnnnc                48

<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
ggacatcaag cagccatgca aatgttaaaa gag                                 33

<210> SEQ ID NO 10
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(30)
<223> OTHER INFORMATION: n = 2-aminopurine
<220> FEATURE:
<221> NAME/KEY: misc_feature
<222> LOCATION: (31)..(31)
<223> OTHER INFORMATION: n = inosine
<220> FEATURE:
<221> NAME/KEY: misc_feature
<222> LOCATION: (32)..(32)
<223> OTHER INFORMATION: n = 2-aminopurine

<400> SEQUENCE: 10
```
ggacatcaag cagccatgca aatgttaann nng                                    33

<210> SEQ ID NO 11
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n= 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (8)..(8)
<223> OTHER INFORMATION: n= 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (12)..(12)
<223> OTHER INFORMATION: n= 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (14)..(14)
<223> OTHER INFORMATION: n= 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (16)..(16)
<223> OTHER INFORMATION: n= 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (46)..(47)
<223> OTHER INFORMATION: n= 2-aminopurine
<220> FEATURE:
<221> NAME/KEY: misc_feature
<222> LOCATION: (48)..(48)
<223> OTHER INFORMATION: n= inosine
<220> FEATURE:
<221> NAME/KEY: misc_feature
<222> LOCATION: (49)..(49)
<223> OTHER INFORMATION: n= 2-aminopurine

<400> SEQUENCE: 11
ctantccncc ancnancgga catcaagcag ccatgcaaat gttaannnng                   50

<210> SEQ ID NO 12
<211> LENGTH: 35
<212> TYPE: DNA
<213> ORGANISM: Artificial Sequence
<220> FEATURE:
<223> OTHER INFORMATION: Synthetic

<400> SEQUENCE: 12
tgctatgtca cttcccttg gttctctcat ctggc                                   35

<210> SEQ ID NO 13
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: n = N4-ethylcytosine
<220> FEATURE:
<221> NAME/KEY: misc_feature
<222> LOCATION: (32)..(32)
<223> OTHER INFORMATION: n = 2-thiothymine

```
<220> FEATURE:
<221> NAME/KEY: misc_feature
<222> LOCATION: (33)..(34)
<223> OTHER INFORMATION: n = inosine

<400> SEQUENCE: 13
tgctatgtca cttccccttg gttctctcat nnnnc                              35

<210> SEQ ID NO 14
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (8)..(8)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (12)..(12)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (14)..(14)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (16)..(16)
<223> OTHER INFORMATION: n = 7-amino-9-(1'-beta-D-2'-
      deoxyribofuranosyl)-imidazo[1,2-c]pyrimidin-5(1H)-one
<220> FEATURE:
<221> NAME/KEY: misc_feature
<222> LOCATION: (48)..(48)
<223> OTHER INFORMATION: n = N4-ethylcytosine
<220> FEATURE:
<221> NAME/KEY: misc_feature
<222> LOCATION: (49)..(49)
<223> OTHER INFORMATION: n = 2-thiothymine
<220> FEATURE:
<221> NAME/KEY: misc_feature
<222> LOCATION: (50)..(51)
<223> OTHER INFORMATION: n = inosine

<400> SEQUENCE: 14
cagnaagngg tngntngtgc tatgtcactt ccccttggtt ctctcatnnn nc           52
```